(12) United States Patent
Pan et al.

(10) Patent No.: US 10,137,072 B2
(45) Date of Patent: Nov. 27, 2018

(54) METHODS AND COMPOSITIONS FOR PROVIDING BROAD SPECTRUM PHOTO PROTECTION USING ANTIOXIDANTS

(71) Applicant: L'OREAL, Paris (FR)

(72) Inventors: Zhi Pan, Ridgewood, NJ (US); Maolin Guo, Dartmouth, MA (US); Jean-Thierry Simonnet, Rueil-Malmaison (FR)

(73) Assignee: L'OREAL, Paris (FR)

( * ) Notice: Subject to any disclaimer, the term of this patent is extended or adjusted under 35 U.S.C. 154(b) by 127 days.

(21) Appl. No.: 15/087,662

(22) Filed: Mar. 31, 2016

(65) Prior Publication Data

US 2017/0281503 A1    Oct. 5, 2017

(51) Int. Cl.
| | | |
|---|---|---|
| A61K 8/00 | (2006.01) | |
| A61K 8/60 | (2006.01) | |
| A61Q 17/04 | (2006.01) | |
| A61K 8/365 | (2006.01) | |
| A61K 8/49 | (2006.01) | |
| A61K 8/97 | (2017.01) | |
| A61K 8/89 | (2006.01) | |
| A61K 8/891 | (2006.01) | |
| A61K 8/35 | (2006.01) | |
| A61K 8/06 | (2006.01) | |

(52) U.S. Cl.
CPC .............. *A61K 8/602* (2013.01); *A61K 8/062* (2013.01); *A61K 8/355* (2013.01); *A61K 8/365* (2013.01); *A61K 8/498* (2013.01); *A61K 8/4926* (2013.01); *A61K 8/4953* (2013.01); *A61K 8/89* (2013.01); *A61K 8/891* (2013.01); *A61K 8/97* (2013.01); *A61Q 17/04* (2013.01); *A61K 2800/592* (2013.01); *A61K 2800/5922* (2013.01)

(58) Field of Classification Search
CPC . A61K 8/33; A61K 8/388; A61K 8/39; A61K 8/445; A61K 8/447; A61K 36/03; A61K 36/05; A61K 47/02; A61Q 5/00; A61Q 19/004; A61Q 7/00; A61Q 17/00; A61Q 19/04; A61Q 5/12
See application file for complete search history.

(56) References Cited

U.S. PATENT DOCUMENTS

| | | | |
|---|---|---|---|
| 4,820,508 A | 4/1989 | Wortzman | |
| 4,828,825 A | 5/1989 | Weber et al. | |
| 8,115,033 B2 | 2/2012 | Koch et al. | |
| 8,263,051 B2 | 9/2012 | Bonda et al. | |
| 9,072,919 B2 | 7/2015 | Pan et al. | |
| 2004/0009197 A1* | 1/2004 | DeRosa | A61K 8/33 424/401 |
| 2008/0213200 A1 | 9/2008 | Vromen | |
| 2009/0208434 A1 | 8/2009 | Schmaus et al. | |
| 2010/0204343 A1 | 8/2010 | Koch et al. | |
| 2012/0015015 A1 | 1/2012 | Kim et al. | |
| 2013/0028854 A1* | 1/2013 | Gupta | A61K 8/347 424/62 |
| 2013/0078205 A1 | 3/2013 | Dayan et al. | |
| 2013/0315846 A1 | 11/2013 | Collier et al. | |
| 2013/0315848 A1 | 11/2013 | Beck et al. | |
| 2013/0324616 A1 | 12/2013 | Beck et al. | |
| 2014/0107046 A1 | 4/2014 | Pan et al. | |
| 2014/0315995 A1 | 10/2014 | Dreher | |

FOREIGN PATENT DOCUMENTS

| | | |
|---|---|---|
| CN | 103221024 A | 7/2013 |
| CN | 103221025 A | 7/2013 |
| CN | 105342973 A | 2/2016 |
| EP | 1263403 A1 | 12/2002 |
| EP | 2545898 A1 | 1/2013 |
| EP | 2642972 A1 | 10/2013 |
| EP | 2642973 A1 | 10/2013 |
| EP | 2679243 A1 | 1/2014 |
| KR | 101516074 B1 | 5/2015 |
| WO | WO-2004050050 A1 | 6/2004 |
| WO | WO-2012069362 A1 | 5/2012 |
| WO | WO-2012069363 A1 | 5/2012 |
| WO | WO-2013007829 A2 | 1/2013 |
| WO | WO-2015/191343 A1 | 12/2015 |

OTHER PUBLICATIONS

PhaMix, Retrieved from URL:https://phamix.com, Baicalin: Nowln Reformulated Anthelios XL SPF 50+ Melt-In Cream, Aug. 17, 2-15 (Year: 2015).*
International Search Report dated Aug. 25, 2017 for corresponding application PCT/US17/24040.

* cited by examiner

*Primary Examiner* — Nannette Holloman
(74) *Attorney, Agent, or Firm* — Polsinelli PC

(57) ABSTRACT

The present disclosure relates to methods and compositions for providing at least broad spectrum photo protection to skin, which includes protection from at least infrared (IR) radiation and/or visible light. The methods typically entail applying to skin a cosmetic composition comprising: (a) one or more antioxidants selected from the group consisting of baicalin, Venuceane™, ferulic acid, polydatin, silymarin, punica granatum extract, mango leaf extract, soliprin, catechin, hesperetin, astilbin, and DHC V; (b) optionally, one or more solubilizers; and (c) a cosmetically acceptable carrier; wherein the combination of (a), optional (b), and (c) alone, provide at least broad spectrum protection from both infrared (IR) radiation and visible light. UV filters can also optionally be included to provide additional protection from UV light.

20 Claims, 2 Drawing Sheets

METHODS AND COMPOSITIONS FOR PROVIDING BROAD SPECTRUM PHOTO PROTECTION USING ANTIOXIDANTS

FIELD OF THE DISCLOSURE

The instant disclosure relates to methods and compositions for providing at least broad spectrum photo protection to skin, which includes protection from infrared (IR) radiation and/or visible light. The methods typically entail applying to skin a unique cosmetic composition comprising one or more antioxidants. The compositions may also optionally include UV filters to provide additional protection from UV light.

BACKGROUND

Skin acts as a natural barrier between internal and external environments and therefore plays an important role in vital biological functions such as protection against mechanical and chemical injury, micro-organisms, and ultraviolet damage. The health and appearance of skin, however, can deteriorate due to environmental factors, genetic makeup, nutrition, and sun exposure.

The negative effects of exposure to ultraviolet ("UV") light are well-known. Prolonged exposure to sunlight causes damage such as sunburn to the skin and dries out hair making it brittle. When skin is exposed to UV light having a wavelength of from about 290 nm to about 400 nm, long term damage can lead to serious conditions such as skin cancer.

UV light also contributes to aging by causing free radicals to form in the skin. Free radicals include, for example, singlet oxygen, hydroxyl radicals, the superoxide anion, nitric oxide and hydrogen radicals. Free radicals attack DNA, membrane lipids and proteins, generating carbon radicals. These in turn react with oxygen to produce a peroxyl radical that can attack adjacent fatty acids to generate new carbon radicals. This cascade leads to a chain reaction producing lipid peroxidation products. Damage to cell membranes results in loss of cell permeability, increased intercellular ionic concentration, and decreased ability to excrete or detoxify waste products. The end result is a loss of skin elasticity and the appearance of wrinkles. This process is commonly referred to as photo-aging.

Although UV radiation can be problematic, over 90% of solar energy is from visible light and infrared (IR) radiation. Visible light and IR radiation, especially IRA (770-1400 nm), penetrates deep into human skin than UV radiation, and can easily reach the dermis. Visible light, especially high energy visible light, can induce pigmentation in a similar manner as UVA, and IR radiation can impair proper functioning of mitochondria. Visible light and IR radiation both contribute to photoaging by degrading collagen through induction of MMP1 enzyme (without induction of the natural endogenous protection MMP1 inhibitor), generating free radicals and decreasing antioxidant content in human skin.

With aging, the outer skin layer (epidermis) thins, even though the number of cell layers remains unchanged. The number of pigment-containing cells (melanocytes), however, decreases. Therefore, the skin appears pale and translucent. Large pigmented spots (age spots, liver spots, or lentigos) may appear in sun-exposed areas. Changes in the connective tissue reduce the skin's strength and elasticity. It is more noticeable in sun-exposed areas (solar elastosis). Elastosis produces the leathery, weather-beaten appearance common to farmers, sailors, and others who spend a large amount of time outdoors. Dehydration increases the risk of skin injury. Poor nutrition can also negatively impact the skin, causing dryness, rash, and puffiness.

SUMMARY OF THE DISCLOSURE

The instant disclosure relates to methods and compositions for providing at least broad spectrum photo protection to skin, which includes protection from infrared (IR) radiation and/or visible light. The methods typically entail applying to skin a unique cosmetic composition comprising one or more antioxidants. The inventors discovered that certain antioxidants and combinations of antioxidants provide unexpected protection from both infrared radiation and visible light and are therefore useful in cosmetic compositions for protecting skin against IR radiation and visible light, in addition to imparting other benefits to the skin, such as improving the health and appearance of skin.

The methods of the instant disclosure typically entail topically applying to the skin of a subject a cosmetic composition comprising: (a) one or more antioxidants selected from the group consisting of baicalin, polydatin, Venuceane™, ferulic acid, silymarin, punica granatum extract, mango leaf extract, hesperetin, Soliprin™, catechin, astilbin, and Dihydroxymethoxy dihydrochalcone (DHC V); (b) optionally, one or more solubilizers; and (c) a cosmetically acceptable carrier; wherein the combination of (a), optional (b), and (c) alone, provide at least broad spectrum protection from both infrared (IR) radiation and/or visible light. In some cases, the one or more antioxidants of (a) includes at least baicalin.

Also, although not required, in many instances, one or more solubilizers of (b) are included in the cosmetic composition. The solubilizers may be, for example, hydrotropes. A non-limiting list of possible hydrotropes includes nicotinamide, caffeine, sodium PCA, sodium salicylate, urea, and hydroxyethyl urea. Further, the compositions of the instant disclosure, in some cases, include (d) one or more emulsifiers, which may be amphoteric, anionic, cationic, nonionic, or a mixture thereof. Moreover, the compositions may be in the form of an emulsion.

Other non-limiting components that can optionally be included in the compositions of the instant disclosure include, for example: (e) one or more UV filters; (f) one or more skin active ingredients; and (g) one or more silicon oils. The one or more UV filters of (e) may be included to provide additional protection from UV light, thereby resulting in a cosmetic compositions providing full spectrum photo protection (protection from IR radiation, visible light, and UV radiation).

Finally, the cosmetic compositions described herein for providing at least broad spectrum photo protection to skin are also useful in other methods, such as methods for: providing anti-aging benefits to the skin; whitening or preventing darkening of skin; improving the appearance of skin; strengthening skin's natural antioxidant defenses; diminishing the visible signs of skin aging; and improving skin's radiance and firmness.

Figure 1:
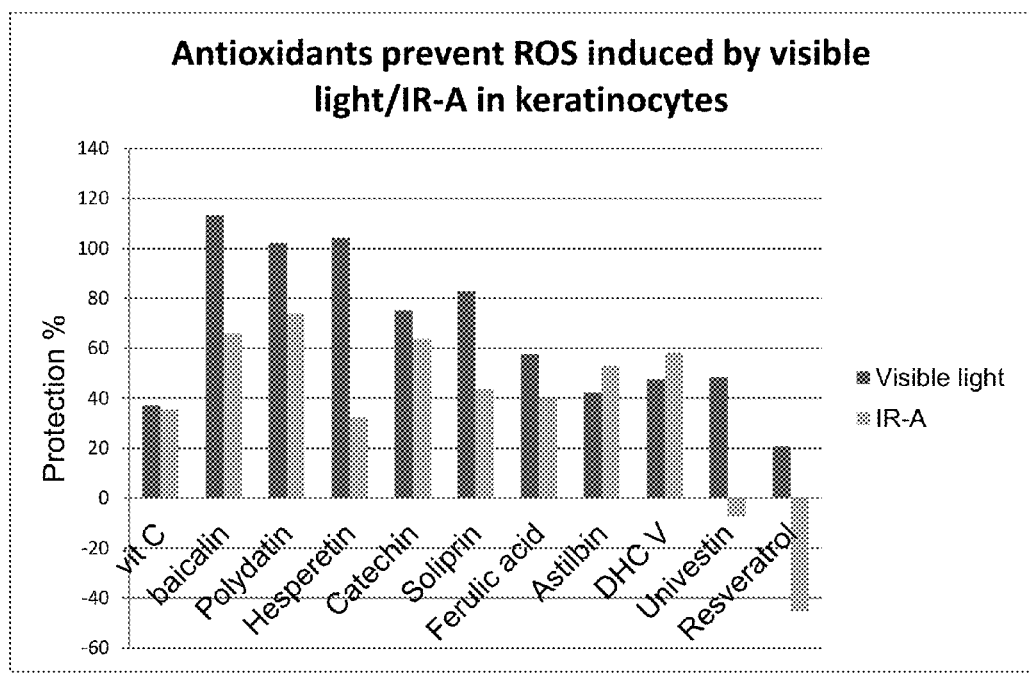
FIG. 1 is a graph showing various antioxidants' ability to prevent reactive oxygen species (ROS) induced by visible light (100 J/cm$^2$) and infrared radiation (200 J/cm$^2$) in keratinocytes.

It should be understood that the various aspects are not limited to the arrangements and instrumentality shown in the figures.

DETAILED DESCRIPTION OF THE DISCLOSURE

The instant disclosure relates to methods and compositions for providing at least broad spectrum photo protection to skin, which includes protection from infrared (IR) radiation and visible light. Typically, the methods entail applying to skin a cosmetic composition comprising: (a) one or more antioxidants selected from the group consisting of baicalin, polydatin, Venuceane™, ferulic acid, silymarin, punica granatum extract, mango leaf extract, hesperetin, Soliprin™, catechin, astilbin, and Dihydroxymethoxy dihydrochalcone (DHC V); (b) optionally, one or more solubilizers; and (c) a cosmetically acceptable carrier; wherein the combination of (a), optional (b), and (c) alone, provide at least broad spectrum protection from both infrared (IR) radiation and visible light.

In some cases, the one or more antioxidants of (a) includes baicalin; and in other cases, the one or more antioxidants of (a) includes polydatin. In some instances, the total amount of the one or more antioxidants in the composition may be from about 0.001 to about 20 wt. % or from about 0.001 to about 20 wt. %, based on the total weight of the composition. Furthermore, the total amount of the one or more antioxidants may be from about 0.001 to about 12 wt. %, about 10 wt. %, about 8 wt. %, about 6 wt. % about 4 wt. %, or about 2 wt. %. Additionally, the total amount of the one or more antioxidants may be from about 0.01 to about 15 wt. %, about 12 wt. %, about 10 wt. %, about 8 wt. %, about 6 wt. %, about 4 wt. %, or about 2 wt. %. Finally, the total amount of the one or more antioxidants may be from about 0.1 to about 15 wt. %, about 12 wt. %, about 10 wt. %, about 8 wt. %, about 6 wt. %, about 4 wt. %, or about 2 wt. %.

In some instances, the compositions include one or more solubilizers (b). Various solubilizers are well known in the art and may be useful for the compositions described herein. In some cases, the one or more solubilizers can be, for example, one or more cosmetically acceptable hydrotopes. A non-limiting list of possible hydrotopes includes nicotinamide, caffeine, sodium PCA, sodium salicylate, urea, and hydroxyethyl urea. The total amount of the one or more hydrotropes in the composition may be about 0.001 wt. % to about 30 wt. %, based on the total weight of the composition. In some instances, the total amount of the one or more hydrotropes in the composition is about 0.001 wt. % to about 25 wt. %, about 20 wt. %, about 15 wt. %, about 14 wt. %, about 12 wt. %, about 10 wt. %, about 8 wt. %, about 6 wt. %, about 4 wt. %, or about 2 wt. %. Likewise, in some instances the total amount of the one or more hydrotopes in the compositions may be about 0.01 wt. % to about 30 wt. %, 25 wt. %, 20 wt. %, 15 wt. %, about 14 wt. % about 12 wt. %, about 10 wt. %, about 8 wt. %, about 6 wt. %, about 4 wt. %, or about 2 wt. %. Moreover, the total amount of the one or more hydrotopes in the composition may be about 0.1 wt. % to about 30 wt. %, 25 wt. %, 20 wt. %, 15 wt. %, about 14 wt. % about 12 wt. %, about 10 wt. %, about 8 wt. %, about 6 wt. %, about 4 wt. %, or about 2 wt. %.

In some instances, if the composition includes at least the hydrotrope hydroxyethyl urea, the maximum amount of the one or more hydrotropes in the composition may be higher than 30 wt. %. For example, if the hydrotrope hydroxyethyl urea is present in the composition, the total amount of the one or more hydrotropes may be (in addition to the ranges already set forth in the above paragraph), from about 1 wt. % to about 60 wt. %, from about 5 wt. % to about 60 wt. %, from about 5 wt. % to about 55 wt. %, from about 5 wt. % to about 50 wt. %, from about 10 wt. % to about 60 wt. %, from about 10 wt. % to about 55 wt. %, from about 10 wt. % to about 50 wt. %, from about 20 wt. % to about 60 wt. %, from about 20 wt. % to about 55 wt. %, from about 20 wt. % to about 50 wt. %, or from about 25 wt. % to about 55 wt. %.

As mentioned previously, the instant compositions typically include a cosmetically acceptable carrier (c), which can also optionally function to help solubilize components of the compositions. For example, the cosmetically acceptable carrier may include water, an organic solvent, or a mixture thereof. Moreover, the cosmetically acceptable carrier may comprise, for example, a hydrophilic organic solvent and/or an amphiphilic organic solvent, wherein the hydrophilic organic solvent is a monohydric $C_1$-$C_8$ alcohol, a polyethylene glycol having from 6 to 80 ethylene oxides, and/or a mono or di-alkyl isosorbide; and the amphiphilic organic solvent is a polypropylene glycol (PPG) and/or a propylene glycol alkyl ester and/or alkyl ether of PPG. Non-limiting examples include ethanol, methanol, PEG 8, propylene glycol, dipropylene glycol, buylene glycol, and isopropyl lauroyl sarccosinate.

In some instances, the compositions of the instant disclosure include one or more emulsifiers (d). Many emulsifiers are known in the art, which may be used in the instant compositions, including, amphoteric, anionic, cationic, and nonionic emulsifiers. Non-limiting examples of nonionic emulsifiers include polyol esters, a glycerol ethers, oxyethylenated and/or oxypropylenated ethers, ethylene glycol polymers, and mixtures thereof. For example, in some cases the emulsifier includes a mixture of a polyol ester and an ethylene glycol polymer, for example, a mixture of glyceryl stearate and PEG-100 stearate. In some instances, an oxyalkylenated organosiloxane emulsifier is included. Non-limiting examples include dimethicone/PEG-10/15 crosspolymer, PEG-15 lauryl dimethicone crosspolymer, PEG-15 lauryl dimethicone crosspolymer, PEG-10 lauryl dimethicone crosspolymer, or a mixture thereof. Accordingly, the compositions of the instant disclosure are often, but not necessarily, in the form of an emulsion.

The total amount of the one or more emulsifiers, when present, may be, for example, about 0.001 to about 10 wt. %, based on the total weight of the composition. In some instances, the total amount of the one or more emulsifiers in the compositions may be about 0.001 wt. % to about 9 wt. %, about 8 wt. %, about 7 wt. %, about 6 wt. %, about 5 wt. %, about 4 wt. %, about 3 wt. %, or about 2 wt. %. Likewise, in some instances the total amount of one or more emulsifers in the compositions may be about 0.01 wt. % to about 9 wt. %, about 8 wt. %, about 7 wt. %, about 6 wt. %, about 5 wt. %, about 4 wt. %, about 3 wt. %, or about 2 wt. %. Additionally, the total amount of the one or more emulsifiers in the compositions may be about 0.1 wt. % to about 9 wt. %, about 8 wt. %, about 7 wt. %, about 6 wt. %, about 5 wt. %, about 4 wt. %, about 3 wt. %, or about 2 wt. %. Finally, the total amount of the one or more emulsifiers in the compositions may be about 0.5 wt. % to about 5 wt. %, about 0.5 wt. % to about 3 wt. %, 0.5 wt. % to about 2 wt. %, or about 1 wt. %.

In some instances, the compositions of the instant disclosure include one or more UV filters (e). Many UV filters are known in the art, which may be used in the instant compositions. The UV filter may be a single UV filter, or a combination of two, three, four, five, or more UV filters, including organic and/or inorganic UV filters. In some instances, the UV filter is an organic UV filter. The one or more UV filters may be selected from the group consisting of a para-aminobenzoic acid derivative, a salicylic derivative, a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, and a mixture thereof.

In some cases, the one or more UV filters is in an amount of from about 0.001 wt. % to about 30 wt. %, about 0.001 to about 20 wt. %, 0.001 to about 10 wt. %, about 0.1 to about 30 wt. %, about 0.1 wt. % to about 25 wt. %, about 0.1 to about 20 wt. %, about 0.1 to about 18 wt. %, 0.1 to about 15 wt. %, about 0.1 to about 12 wt. %, about 0.1 to about 10 wt. %, 0.1 to about 8 wt. %, about 0.1 to about 6 wt. %, about 1 wt. % to about 30 wt. %, about 0.1 wt. % to about 25 wt. %, about 1 wt. % to about 20 wt. %, about 1 wt. % to about 18 wt. %, about 1 wt. % to about 15 wt. %, about 1 wt. % to about 12 wt. %, about 1 wt. % to about 10 wt. %, about 1 wt. % to about 8 wt. %, about 1 wt. % to about 6 wt. %, about 5 wt. % to about 30 wt. %, about 5 wt. % to about 25 wt. %, about 5 wt. % to about 20 wt. %, about 5 wt. % to about 18 wt. %, about 5 wt % to about 15 wt. %, about 5 wt. % to about 12 wt. %, about 5 wt. % to about 10 wt. %, about 5 wt. % to about 8 wt. %, or from about 3 wt. % to about 20 wt. %, wherein the weight percent is based on the total weight of the sunscreen composition.

In some instances, the compositions of the instant disclosure include one or more skin active ingredients (f). For example, the skin active ingredient may be a humectant, a moisturizing ingredient, an anti-aging agent, a depigmenting agent, an anti-wrinkle agent, an agent that treats oily skin, and a mixture thereof. In some cases, the one or more skin active ingredients may be adenosine, ascorbic acid, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, a coenzyme, or a mixture thereof.

The amount of the skin active ingredients may be individually or combination from about 0.001 to about 10 wt. %, based on the total weight of the composition. In some instances, the amount of the skin active ingredients may be individual or combination from about 0.001 wt. % to about 9 wt. %, about 8 wt. %, about 7 wt. %, about 6 wt. %, about 5 wt. %, about 4 wt. %, about 3 wt. %, or about 2 wt. %. Likewise, in some instances the amount of the skin active ingredients may be individual or combination from about 0.01 wt. % to about 9 wt. %, about 8 wt. %, about 7 wt. %, about 6 wt. %, about 5 wt. %, about 4 wt. %, about 3 wt. %, or about 2 wt. %. Additionally, the amount of the skin active ingredients may be individual or combination from 0.1 wt. % to about 9 wt. %, about 8 wt. %, about 7 wt. %, about 6 wt. %, about 5 wt. %, about 4 wt. %, about 3 wt. %, or about 2 wt. %. Finally, the amount of the skin active ingredients may be individual or combination from about 0.5 wt. % to about 5 wt. %, about 0.5 wt. % to about 3 wt. %, 0.5 wt. % to about 2 wt. %, or about 1 wt. %.

In some instances, the compositions of the instant disclosure include one or more silicon oils (g). For example, the one or more silicon oils may be selected from the group consisting of polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl (trimethylsiloxy)diphenylsiloxanes, diphenyl dimethicones, diphenyl(methyldiphenyl)trisiloxanes, (2-phenylethyl) trimethyl siloxysilicates, and a mixture thereof. In some cases, the one or more silicon oils comprises dimethicone. The total amount of the one or more silicon oils may be, for example, from about 0.1 wt. % to about 40 wt. %, about 35 wt. %, about 30 wt. %, about 25 wt. %, about 20 wt. %, about 15 wt. %, about 10 wt. %, about 5 wt. %, about 4 wt. %, about 3 wt. %, or about 2 wt. %. In some cases, the total amount of silicon oil may be from about 0.1 wt. %, about 0.5 wt. %, about 1 wt. %, about 2 wt. %, about 3 wt. %, about 4 wt. %, about 5 wt. %, about 10 wt. %, about 15 wt. % to about 40 wt. %.

In some cases, the compositions of the instant disclosure may include vitamin E. The total amount of the vitamin E of in the compositions may be about 0.001 to about 10 wt. %, based on the total weight of the composition. In some instances, the total amount of vitamin E in the compositions may be about 0.001 wt. % to about 9 wt. %, about 8 wt. %, about 7 wt. %, about 6 wt. %, about 5 wt. %, about 4 wt. %, about 3 wt. %, or about 2 wt. %. Likewise, in some instances the total amount of vitamin E in the compositions may be about 0.01 wt. % to about 9 wt. %, about 8 wt. %, about 7 wt. %, about 6 wt. %, about 5 wt. %, about 4 wt. %, about 3 wt. %, or about 2 wt. %. Additionally, the total amount of vitamin E in the compositions may be about 0.1 wt. % to about 9 wt. %, about 8 wt. %, about 7 wt. %, about 6 wt. %, about 5 wt. %, about 4 wt. %, about 3 wt. %, or about 2 wt. %.

Finally, the instant disclosure relates to methods of using the compositions described herein, for example, in the treatment of skin (in addition to providing at least broad spectrum photo protection to the skin). For example, the compositions may be used in methods for: providing anti-aging benefits to the skin; whitening or preventing darkening of skin; improving the appearance of skin; strengthening skin's natural antioxidant defenses; diminishing the visible signs of skin aging; and improving skin's radiance and firmness. These methods typically entail applying the compositions described herein to the skin.

More exhaustive but non-limiting lists of components useful in the instant compositions disclosed herein are presented below.

Solubilizers

The solubilizers are typically compounds or groups of compounds that help solubilize the resveratrol, the polydatin, and/or the baicalin in the compositions of the instant disclosure. One or more solubilizers may be a hydrotrope, but the solubilizers are not required to be hydrotropes. Hydrotropes (or hydrotropic agents) are a diverse class of water-soluble compounds that are characterized by an amphiphilic molecular structure and an ability to dramatically increase the solubility of poorly soluble organic molecules in water.

Many hydrotropes have an aromatic structure with an ionic moiety, while some of them are linear alkyl chains. Although hydrotropes noticeably resemble surfactants and have the ability to reduce surface tension, their small hydrophobic units and relatively shorter alkyl chain distinguish them as a separate class of amphiphiles. Consequently their hydrophobicity is not sufficient enough to create well organized self-associated structures, such as micelles, even with a high concentration.

Common hydrotropic molecules include: sodium 1,3-benzenedisulfonate, sodium benzoate, sodium 4-pyridinecarboxylate, sodium salicylate, sodium benzene sulfonate, caffeine, sodium p-toluene sulfonate, sodium butyl monoglycolsulfate, 4-aminobenzoic acid HCl, sodium cumene sulfonate, N,N-diethylnicotinamide, N-picolylnicotinamide, N-allylnicotinamide, 2-methacryloyloxyethyl phosphorylcholine, resorcinol, butylurea, pyrogallol, N-picolylacetamide 3.5, procaine HCl, proline HCl, nicotinamide, pyridine, 3-picolylamine, sodium ibuprofen, sodium xylenesulfonate, ethyl carbamate, pyridoxal hydrochloride, sodium benzoate, 2-pyrrolidone, ethylurea, N,N-dimethylacetamide, N-methylacetamide, and isoniazid. Hydrotropes can be found in Lee J. et al., "Hydrotropic Solubilization of Paclitaxel: Analysis of Chemical Structures for Hydrotropic Property", Pharmaceutical Research, Vol. 20, No. 7, 2003; and Lee S. et al., "Hydrotropic Polymers: Synthesis and Characterization of Polymers Containing Picolylnicotinamide Moieties", Macromolecules, 36, 2248-2255, 2003. Additional hydrotropes include nicotinamide (Vit B3), caffeine, sodium PCA, sodium salicylate, urea, an dhydroxyethyl urea.

Cosmetically Acceptable Carrier

Cosmetically acceptable carriers include, but are not limited to, one or more aqueous systems, glycerin, $C_{1-4}$ alcohols, organic solvents, fatty alcohols, fatty ethers, fatty esters, polyols, glycols, vegetable oils, mineral oils, liposomes, laminar lipid materials, water, or any combinations thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

In some instances, cosmetically acceptable carriers may comprise water, a mixture of water and at least one cosmetically acceptable organic solvent, or at least one cosmetically acceptable organic solvent. Additionally, cosmetically acceptable carriers may be or may include ethanol, a glycol ether, for example, dipropylene glycol n-butyl ether, isododecane, mineral oil, propylene glycol, pentylene glycol, hexylene glycol, glycerol, and mixtures thereof.

Emulsifiers

Emulsifiers are well known in the art and include amphoteric, anionic, cationic or nonionic emulsifiers, used alone or as a mixture, and optionally with a co-emulsifier. The emulsifiers are chosen in an appropriate manner according to the emulsion to be obtained.

For W/O emulsions, examples of emulsifiers that may be mentioned include dimethicone copolyols, such as the mixture of cyclomethicone and dimethicone copolyol sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM90™ by the company Goldschmidt.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

In some instance, the one or more emulsifiers include an oganosiloxane emulsifier, including crosslinked organosiloxane emulsifiers. For example, the compositions may comprise one or more crosslinked organosiloxane emulsifier selected from the group consisting of dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer.

In another embodiment, the compositions include one or more linear organosiloxane emulsifier selected from the group consisting of cyclotetrasiloxane (and) cyclopentasiloxane (and) PEG/PPG-18 dimethicone, cyclopentasiloxane (and) PEG/PPG-18/18 dimethicone; PEG/PPG-18/18 dimethicone; lauryl PEG/PPG-18/18 methicone; cetyl PEG/PPG-14/14 dimethicone; bis-cetyl PEG/PPG-14/14 dimethicone; cetyl PEG/PPG-10/1 dimethicone; PEG-11 methyl ether dimethicone; PEG/PPG-20/22 butyl ether dimethicone; PEG-9 dimethicone; PEG-3 dimethicone; PEG-9 methyl ether dimethicone; PEG-10 dimethicone; lauryl PEG-9 polydimethylsiloxyethyl dimethicone.

Usable oxyalkylenated organosiloxane emulsifier include the following:

An oxyalkylenated organosiloxane emulsifier having the general formula:

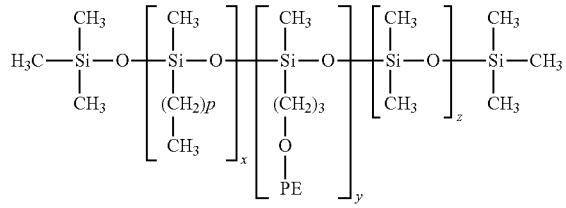

wherein p is 0-40 (the range including all numbers between and subranges such as 2, 3, 4, 13, 14, 15, 16, 17, 18, etc.), and PE is $(-C_2H_4O)_a-(-C_3H_6O)_b-H$ wherein a is 0-25, b is 0-25 with the proviso that both a and b cannot be 0 simultaneously, x, y, and z are each independently ranging from 0 to 1 million with the proviso that x and y cannot be 0 simultaneously. In some cases, x, y, z, a, and b are such that the molecular weight of the polymer ranges from about 5,000 to about 500,000, from about 10,000 to 100,000, or is about 50,000, and the polymer is generically referred to as dimethicone copolyol. In some instances, p is such that the long chain alkyl is cetyl or lauryl, and the compound is called, generically, cetyl dimethicone copolyol or lauryl dimethicone copolyol respectively. In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or ether, such as methyl ether, ethyl ether, propyl ether, butyl ether, and the like.

An oxyalkylenated organosiloxane emulsifier having the general formula:

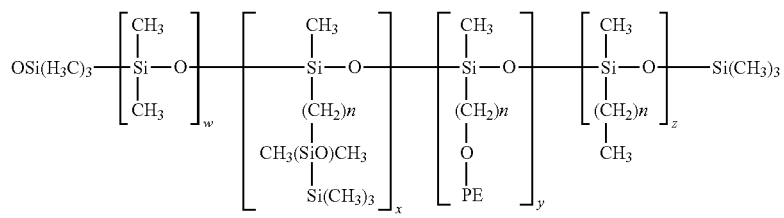

wherein each n is independently 0-100 with the proviso that there must be at least one PE radical. In some instances, where each n independently ranges from about 2 to 30, and PE $(-C_2H_4O)_a-(-C_3H_6O)_b-$H wherein a is 0-25, b is 0-25 with the proviso that both a and b cannot simultaneously be 0; and wherein w, x, y, and z are each independently 0 to 1,000,000 with the proviso that there is at least one PE. In some embodiments the organosiloxane emulsifier is lauryl PEG-9 Polydimethylsiloxyethyl Dimethicone. Oxyalkylenated organosiloxane emulsifiers disclosed in U.S. Pat. No. 9,095,543 are useful in the instant compositions. U.S. Pat. No. 9,095,543 is incorporated herein by reference in its entirety.

Further examples of organosiloxane emulsifiers include those having C.T.F.A. names Bis-Butyldimethicone Polyglyceryl-3; Bis-PEG/PPG-14/14 Dimethicone; Bis-butyldimethicone Polyglyceryl-3; Bis-isobutyl PEG/PPG-10/7 Dimethicone copolymer; Bis-PEG/PPG-18/6 Dimethicone; Bis-PEG/PPG-20/20 Dimethicone; Bis-PEG/PPG-16/16 PEG/PPG-16/16 Dimethicone; Bis(PPG-7 Undeceneth-21-Dimethicone; Cetyl Dimethicone PEG-7 Acetate; Cetyl PEG-8 Dimethicone; Cetyl PEG/PPG-15/16 Butyl Ether Dimethicone; Cetyl PEG/PPG-15/15 Butyl Ether Dimethicone; Cetyl PEG/PPG-7/3 Dimethicone; Cetyl PEG/PPG-10/1 Dimethicone; Dimethicone PEG-15 Acetate; Dimethicone PEG-7 Cocoate; Dimethicone PEG-7 Phosphate; Dimethicone PEG-10 Phosphate; Dimethicone PEG/PPG-7/4 Phosphate; Dimethicone PEG/PPG-12/4 Phosphate; Dimethicone PEG-7 Undecylenate; Lauryl Dimethicone PEG-10 Phosphate; Isopolyglyceryl-3 Dimethicone; Isopolyglyceryl-3 Dimethiconol; Isostearyl Carboxyldecyl PEG-8 Dimethicone; Lauryl Methicone PEG-10 Phosphate; Lauryl PEG-8 Dimethicone; Lauryl PEG-10 Methyl Ether Dimethicone; Lauryl PEG/PPG-18/18 Methicone; PEG-6 Methyl Ether Dimethicone; PEG-7 Methyl Ether Dimethicone; PEG-9 Methyl Ether Dimethicone; PEG-10 Methyl Ether Dimethicone; PEG-11 Methyl Ether Dimethicone; PEG-11 Methyl Ether Dimethicone; PEG-32 Methyl Ether Dimethicone; PEG-PEG/PPG-28/21 Acetate Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-3/10 Dimethicone; PEG/PPG-4/12 Dimethicone; PEG/PPG-6/11 Dimethicone; PEG/PPG-8/14 Dimethicone; PEG/PPG-12/16 Dimethicone; PEG/PPG-12/18 Dimethicone; PEG/PPG-14/4 Dimethicone; PEG/PPG-15/5 Dimethicone; PEG/PPG-15/15 Dimethicone; PEG/PPG-16/2 Dimethicone; PEG/PPG-16/8 Dimethicone; PEG/PPG-17/18 Dimethicone; PEG/PPG-18/12 Dimethicone; PEG/PPG-19/19 Dimethicone; PEG/PPG-20/6 Dimethicone; PEG/PPG-20/15 Dimethicone; PEG/PPG-20/20 Dimethicone; PEG/PPG-20/29 Dimethicone; PEG/PPG-22/23 Dimethicone; PEG/PPG-22/24 Dimethicone; PEG/PPG-25/25 Dimethicone; PEG/PPG-27/27 Dimethicone; PEG/PPG-30/10 Dimethicone; PEG/PPG-10/3 Oleyl Ether Dimethicone; PEG-8 trisiloxane; Polyglyceryl-3 Polydimethylsiloxyethyl Dimethicone; PPG-12 Butyl Ether Dimethicone; Silicone Quaternium-17; TEA-Dimethicone PEG-7 Phosphate; or mixtures thereof.

Further examples of commercial linear organosiloxane emulsifiers are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of fully or partially crosslinked oxyalkylenated organosiloxane emulsifiers. They may be elastomeric or non-elastomeric. They are sometimes referred to as "emulsifying elastomers" because of they have both elastomeric and emulsifying properties.

Polyoxyalkylenated silicone elastomers that may be used in at least one embodiment include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone;

KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers include dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

Further examples of crosslinked organosiloxane emulsifiers include, but are not limited to Dimethicone/dimethicone PEG/PPG 15 crosspolymer; Dimethicone PEG-10 crosspolymer; Dimethicone PEG-10/15 Crosspolymer; Dimethicone PEG-15 Crosspolymer; Dimethicone Polyglycerin-3 Crosspolymer; Dimethicone PPG-20 Crosspolymer; Dimethiconol/Methylsilanol/Silicate Crosspolymer; Dimethiconol/Silicate Crosspolymer; Lauryl Dimethicone PEG-15 Crosspolymer; Lauryl Dimethicone Polyglycerin-3 Crosspolymer; PEG-8 Dimethicone Polysorbate-20 Crosspolymer; PEG-10 DimethiconeNinyl Dimethicone Crosspolymer; PEG-10 Lauryl Dimethicone Crosspolymer; PEG-15/Lauryl Dimethicone Crosspolymer; and PEG-15 Laurylpolydimethylsiloxyethyl Crosspolymer.

UV Filters

UV filters are well known in the art for their use in stopping UV radiation. For example, the UV filter may be one or more organic UV filters and/or one or more inorganic UV filters. Non-limiting examples of UV filters include:
i. Sparingly soluble UV filters (not appreciably soluble in either water or oil) such as Methylene Bis-Benzotriazolyl Tetramethylbutylphenol, Tris-Biphenyl Triazine, Methanone, 1,1'-(1,4-piperazinediyl)bis[1-[2-[4-(diethylamino)-2-hydroxybenzoyl]phen-yl]- and mixtures thereof.
ii. Oil soluble organic UV filters (at least partially soluble in oil or organic solvent), such as Bis-Ethylhexyloxyphenol Methoxyphenyl Triazine, Butyl Methoxydibenzoylmethane (BMBM), Oxybenzone, Sulisobenzone, Diethylhexyl Butamido Triazone (DBT), Drometrizole Trisiloxane, Ethylhexyl Methoxycinnamate (EHMC), Ethylhexyl Salicylate (EHS), Ethylhexyl Triazone (EHT), Homosalate, Isoamyl p-Methoxycinnamate, 4-Methylbenzylidene Camphor, Octocrylene (OCR), Polysilicone-15, and Diethylamino Hydroxy Benzoyl Hexyl Benzoate (DHHB);
iii. Inorganic UV filters such as titanium oxide and zinc oxide, iron oxide, zirconium oxide and cerium oxide; and
iv. Water soluble UV filters such as Phenylbenzimidazole Sulfonic Acid (PBSA), Sulisobenzone-sodium salt, Benzydilene Camphor Sulfonic Acid, Camphor Benzalkonium Methosulfate, Cinoxate, Disodium Phenyl Dibenzylmidazole Tetrasulfonate, Terephthalylidene Dicamphor Sulfonic Acid, PABA, and PEG-25 PABA.

In some instances, the UV filter is one or more of: a para-aminobenzoic acid derivative, a salicylic derivative, a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, or a mixture thereof.

Suitable UV filters can include UV filters that protect against both UVA and UVB radiation, or UV filters that protect against UVA or UVB radiation. In some instances, the one or more UV filters may be methylene bis-benzotriazolyl tetramethylphenol, diethylamino hydroxybenzoyl hexyl benzoate, coated or uncoated zinc oxide, ethylhexyl methoxycinnamate, isoamyl methoxycinnamate, homosalate ethyl hexyl salicilate, octocrylene, polysilicone-15, butyl methoxydibenzoylmethane, menthyl anthranilate, and ethylhexyl dimethyl PABA.

Furthermore, combinations of UV filters may be used. For example, the combination of UV filters may be octocrylene, avobenzone (butyl methoxydibenzoylmethane), oxybenzone (benzophenone-3), octisalate (ethylhexyl salicylate), and homosalate, as described in application Ser. No. 13/304,195, which is incorporated herein by reference in its entirety. For instance, this combination of UV filters may be used in the following ratios relative to avobenzone:
the ratio of octocrylene to avobenzone is 1.6:1.0 to 2.4:1.0;
the ratio of oxybenzone to avobenzone 1.0:1.0 to 1.6:1.0;
the ratio of octisalate to avobenzone is 0.8:1.0 to 1.3:1.0; and
the ratio of homosalate to avobenzone is 2.8:1.0 to 4.3:1.

Furthermore, the ratio of each UV filter relative to avobenzone may be about: 2.0:1.0:1.3:1.1:3.6 (octocrylene:avobenzone:oxybenzone:octisalate:homosalate).

In another embodiment, the at least one UV filter is a combination of UV filters comprising octocrylene, avobenzone, octisalate, and homosalate, and optionally oxybenzone, as described in application Ser. No. 13/304,202, which is incorporated herein by reference in its entirety. For instance, this combination of UV filters may be used in the following ratios relative to avobenzone:
the ratio of octocrylene to avobenzone is 1.6:1.0 to 2.4:1.0,
the ratio of oxybenzone to avobenzone 0.0:1.0 to 0.016:1.0,
the ratio of octisalate to avobenzone is 1.3:1.0 to 2.0:1.0, and
the ratio of homosalate to avobenzone is 2.3:1.0 to 3.6:1.

Furthermore, the ratio of each UV filter relative to avobenzone may be about: 2.0:1.0:0.0:1.7:3.0 (octocrylene:avobenzone:oxybenzone:octisalate:homosalate).

In another embodiment, the at least one UV filter is a combination of UV filters comprising octocrylene, butyl methoxydibenzoylmethane, bis-ethylhexyloxyphenol methoxyphenyl triazine, ethylhexyl triazone, terephthalylidene dicamphor sulfonic acid, and drometrizole trisiloxane, as described in application Ser. No. 13/719,328, which is incorporated herein by reference in its entirety. For instance, this combination of UV filters may be used in the following ratios relative to butyl methoxydibenzoylmethane:
the ratio of octocrylene to butyl methoxydibenzoylmethane is 0.8:1.0 to 1.5:1.0;
the ratio of bis-ethylhexyloxyphenol methoxyphenyl triazine to butyl methoxydibenzoylmethane 0.3:1.0 to 0.8:1.0;
the ratio of ethylhexyl triazone to butyl methoxydibenzoylmethane is 0.3:1.0 to 1.0:1.0;
the ratio of terephthalylidene dicamphor sulfonic acid to butyl methoxydibenzoylmethane is 0.1:1.0 to 0.5:1.0; and the ratio of drometrizole trisiloxane to butyl methoxy-dibenzoylmethane is 0.3:1.0 to 1.0:1.0.

Furthermore, the ratio of each UV filter relative to butyl methoxydibenzoyl-methane may be about: 1.2:1.0:0.5:0.6:0.4:0.6 (octocrylene:butyl methoxy-dibenzoylmethane:bis-ethylhexyloxyphenol methoxyphenyl triazine:ethylhexyl triazone:terephthalylidene dicamphor sulfonic acid:drometrizole trisiloxane).

In another embodiment, the at least one UV filter is a combination of UV filters comprising octocrylene, butyl methoxydibenzoylmethane, ethylhexyl triazone, terephthalylidene dicamphor sulfonic acid, and drometrizole trisiloxane, as described in application Ser. No. 13/719,351, which is incorporated herein by reference in its entirety. For instance, this combination of UV filters may be used in the following ratios relative to butyl methoxydibenzoylmethane:

the ratio of octocrylene to butyl methoxydibenzoylmethane is 0.6:1.0 to 1.25:1.0;
the ratio of ethylhexyl triazone to butyl methoxydibenzoylmethane is 0.4:1.0 to 1.0:1.0;
the ratio of terephthalylidene dicamphor sulfonic acid to butyl methoxydibenzoylmethane is 0.3:1.0 to 0.7:1.0; and
the ratio of drometrizole trisiloxane to butyl methoxy-dibenzoylmethane is 0.4:1.0 to 1.1:1.0.

Furthermore, the ratio of each UV filter relative to butyl methoxydibenzoyl-methane may be about: 1.0:1.0:0.7:0.5:0.7 (octocrylene:butyl methoxydibenzoylmethane:ethylhexyl triazone:terephthalylidene dicamphor sulfonic acid:drometrizole trisiloxane).

In another embodiment, the at least one UV filter is a combination of UV filters comprising octocrylene, butyl methoxydibenzoylmethane, bis-ethylhexyloxyphenol methoxyphenyl triazine, terephthalylidene dicamphor sulfonic acid, and drometrizole trisiloxane, as described in application Ser. No. 13/719,368, which is incorporated herein by reference in its entirety. For instance, this combination of UV filters may be used in the following ratios relative to butyl methoxydibenzoylmethane:

the ratio of octocrylene to butyl methoxydibenzoylmethane is 0.8:1.0 to 1.2:1.0;
the ratio of bis-ethylhexyloxyphenol methoxyphenyl triazine to butyl methoxydibenzoylmethane is 0.2:1.0 to 0.6:1.0;
the ratio of terephthalylidene dicamphor sulfonic acid to butyl methoxydibenzoylmethane is 0.0.25:1.0 to 0.75:1.0; and
the ratio of drometrizole trisiloxane to butyl methoxy-dibenzoylmethane is 0.4:1.0 to 0.8:1.0.

Furthermore, the ratio of each UV filter relative to butyl methoxydibenzoyl-methane may be about: 1.0:1.0:0.4:0.4:0.6 (octocrylene:butyl methoxydibenzoylmethane:bis-ethylhexyloxyphenol methoxyphenyl triazine:terephthalylidene dicamphor sulfonic acid:drometrizole trisiloxane).

In another embodiment, the at least one UV filter is a combination of UV filters comprising octocrylene, butyl methoxydibenzoylmethane, bis-ethylhexyloxyphenol methoxyphenyl triazine, terephthalylidene dicamphor sulfonic acid, and drometrizole trisiloxane, as described in application Ser. No. 13/719,374, which is incorporated herein by reference in its entirety. For instance, this combination of UV filters may be used in the following ratios relative to butyl methoxydibenzoylmethane is as follows:

the ratio of octocrylene to butyl methoxydibenzoylmethane is 0.8:1.0 to 1.3:1.0;
the ratio of bis-ethylhexyloxyphenol methoxyphenyl triazine to butyl methoxydibenzoylmethane is 0.1:1.0 to 0.6:1.0;
the ratio of ethylhexyl triazone to butyl methoxydibenzoylmethane is 0.2:1.0 to 0.6:1.0; and
the ratio of drometrizole trisiloxane to butyl methoxy-dibenzoylmethane is 0.3:1.0 to 0.7:1.0. [Synergistic combination from PR2012573]

Furthermore, the ratio of each UV filter relative to butyl methoxydibenzoyl-methane may be about: 1.0:1.0:0.3:0.5:0.5 (octocrylene:butyl methoxydibenzoylmethane:bis-ethylhexyloxyphenol methoxyphenyl triazine:ethylhexyl triazone:drometrizole trisiloxane).

In another embodiment, the at least one UV filter is a combination of UV filters comprising octocrylene, butyl methoxydibenzoylmethane, bis-ethylhexyloxyphenol methoxyphenyl triazine, terephthalylidene dicamphor sulfonic acid, and terephthalylidene dicampohor sulfonic acid, as described in application Ser. No. 13/719,393, which is incorporated herein by reference in its entirety. For instance, this combination of UV filters may be used in the following ratios relative to butyl methoxydibenzoylmethane is as follows:

the ratio of octocrylene to butyl methoxydibenzoylmethane is 0.8:1.0 to 1.6:1.0;
the ratio of bis-ethylhexyloxyphenol methoxyphenyl triazine to butyl methoxydibenzoylmethane is 0.2:1.0 to 0.6:1.0;
the ratio of ethylhexyl triazone to butyl methoxydibenzoylmethane is 0.3:1.0 to 0.6:1.0; and
the ratio of terephthalylidene dicampohor sulfonic acid to butyl methoxydibenzoylmethane is 0.01:1.0 to 0.3:1.0.

Furthermore, the ratio of each UV filter relative to butyl methoxydibenzoyl-methane may be about: 1.2:1.0:0.3:0.5:0.1 (octocrylene:butyl methoxydibenzoylmethane:bis-ethylhexyloxyphenol methoxyphenyl triazine:ethylhexyl triazone:terephthalylidene dicampohor sulfonic acid).

Silicon Oils

Non-limiting examples of silicone oils include dimethicone, cyclomethicone, polysilicone-11, phenyl trimethicone, trimethylsilylamodimethicone, and stearoxytrimethylsilane. In some cases, the cosmetic composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

Other examples of silicone oils that may be mentioned include volatile linear or cyclic silicone oils, especially those with a viscosity 8 centistokes ($8 \times 10^6$ m$^2$/s) and especially containing from 2 to 7 silicon atoms, these silicones optionally comprising alkyl or alkoxy groups containing from 1 to 10 carbon atoms. As volatile silicone oils that may be used in the disclosure, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Implementation of the present disclosure is provided by way of the following examples. The examples serve to illustrate the technology without being limiting in nature.

EXAMPLES

Example 1

A sensitive in vitro ROS (Reactive Oxygen Species) probe was used to evaluate the protective effects of antioxidants on live skin cells against visible light and infrared radiation (IR). Based on a blind screening of 26 compounds, 12 compounds were discovered that efficiently (>40%) decrease the ROS induced by visible light and/or IR radiation on human skin keratinocytes and/or fibroblasts. These compounds (or mixtures of these compounds) provide biological protection for skin cells against visible light and infrared radiation.

Figure 2:
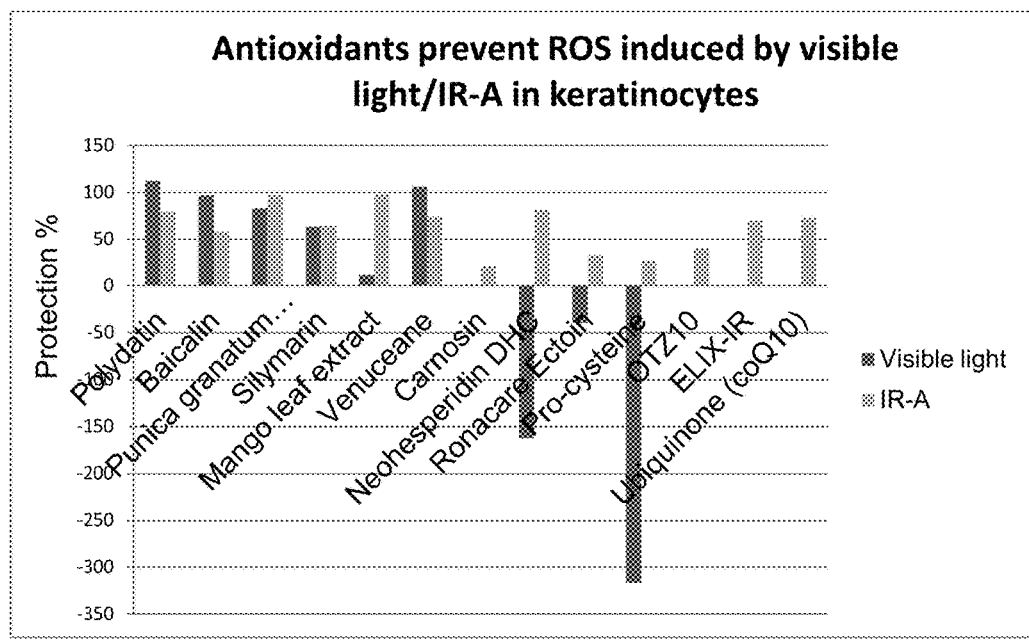
FIG. 2 is an extension of the graph of FIG. 1 showing additional antioxidants' ability to prevent reactive oxygen species (ROS) induced by visible light (100 J/cm$^2$) and infrared radiation (200 J/cm$^2$) in keratinocytes.

Human cells were pre-treated with and without antioxidants for 24 hours at a very low concentration (10 µg/ml (0.001%)). After incubation for 24 hours, the cells were rinsed and the medium changed in order to remove all the antioxidants before light exposure. The cells were exposed to visible light (100 J/cm$^2$) and infrared radiation (200 J/cm$^2$) using Xenon Light Source 300W Monochromatic Light with Filters Max-303 (Asashi Spectra company). After exposure to the visible light and the IR radiation, a new ROS probe was incubated with the cells for one hour to track the in vitro ROS produced. A comfocal microscope and associated software was used to image the fluorescent signals from individual cells and quantify the fluorescence intensity. By comparing with control samples without a pretreatment of antioxidants, it was possible to quantify the protection effect. A summary of the results is provided in the table below and the results are graphically presented in FIG. 1 and FIG. 2.

| Antioxidant | Visible light protection % | IR protection % |
|---|---|---|
| Baicalin | Strong | Medium |
| Neohesperidin DHC | Negative | Strong |
| Phloretin | | Negative |
| Carnosin | Low | Low |
| Ronacare Ectoin | Negative | Low |
| Venuceane ™ | Strong | Strong |
| Pro-cysteine | Negative | Low |
| Vit C | Low | Low |
| Resveratrol | Low | Negative |
| Ferulic Acid | Medium | Medium |
| Polydatin | Strong | Strong |
| Silymarin | Medium | Medium |
| Origa'light | | Negative |
| OTZ10 | NA | Medium |
| ELIX-IR | NA | Strong |
| Magui berry extract | Negative | — |
| Punica granatum extract | Strong | Strong |
| Mango leaf extract | Low | Strong |
| Ubiquinone(coQ10) | NA | Strong |
| licochalcone A | | Negative |
| Soliprin | Strong | Medium |
| Univestin | Medium | Negative |
| Catechin | Strong | Medium |
| Hesperetin | Strong | Low |
| Astilbin | Medium | Medium |
| DHC V | Medium | Medium |

In the table above, "strong" refers to a percent protection greater than 70%, "Medium" refers to a percent protection less than or equal to 70% but greater than or equal to 40%. "Low" refers to a percent protection less than 40%. The term "negative" is used when there is no protection. The results presented in the table above are also graphically shown in FIG. 1 and FIG. 2. The protection percentage was defined according to the equation below (wherein the term "AOX" refers to "antioxidant").

$$\text{Protection \%} = \frac{ROS_{light\ exposure} - ROS_{AOX+light\ exposure}}{ROS_{light\ exposure} - ROS_{no\ light\ exposure}} \times 100\%$$

Since the in vitro tests were done on live human skin cells, kerotinocytes and fibroblasts, and the antioxidants in the cell culture media were removed before light exposure, the results directly predict the biological protection effects of the antioxidants on skin against visible light and infrared radiation. This was further confirmed by the absorption spectrum of these antioxidants, which showed no absorption in the visible light and infrared radiation area.

Example 2

Serum

A serum was prepared containing the antioxidant silymarin. The components of the serum are shown in the table below.

| | Antioxidant (Silymarin) | |
|---|---|---|
| Phase | Ingredient | Amount |
| A | Dipropylene Glycol | 10 |
| | Propylene Glycol | 10 |
| | Denatured Alcohol | 10 |
| | Silymarin (antioxidant) | 0.5 |
| B | Water | 66.5 |
| | Laureth-23 | 3 |

The components of Phase A except for the alcohol were combined and mixed at 60° C. then cooled to room temperature. Once at room temperature, the alcohol was added. The components of Phase B were separately combined and mixed. The mixture was heated to 65° C. in order to dissolve the laureth-23. Phase A was added into phase B and mixed until the composition had a uniform consistency.

Example 3

Serum

A serum was prepared containing the antioxidants baicalin and polydatin and the hydrotropes niacinamide and caffeine. The components of the serum are shown in the table below.

| | Antioxidants (Baicalin and Polydatin) with Hydrotropes (Niacinamide and Caffeine) | |
|---|---|---|
| Phase | Ingredient | Amount |
| A | Dipropylene Glycol | 10 |
| | Propylene Glycol | 10 |
| | Denatured Alcohol | 10 |
| | Vitamin E | 1 |
| B | Water | 50 |

-continued

| Antioxidants (Baicalin and Polydatin) with Hydrotropes (Niacinamide and Caffeine) | | |
|---|---|---|
| Phase | Ingredient | Amount |
| | Niacinamide (hydrotrope) | 5 |
| | Caffeine (hydrotrope) | 5 |
| | Laureth-23 | 5 |
| | Baicalin (antioxidant) | 1 |
| | Polydatin (antioxidant) | 3 |

The components of Phase A were combined and mixed at room temperature. The components of Phase B except for the baicalin and polydatin were combined and mixed until the niacinamide and caffeine were completely dissolved. Then the baicalin and polydatin were added. Phase B was then heated to 65° C. in order to dissolve the laureth-23. Phase A was then added into Phase B while mixing. The combination was mixed for at least 30 minutes.

Example 4

Oil-in-Water Emulsion without SPF

Oil-in-water emulsions containing the antioxidants baicalin and polydatin and the hydrotropes niacinamide and caffeine are presented in the table below.

| Antioxidants (Baicalin and Polydatin) with Hydrotropes (Niacinamide and Caffeine) | | | |
|---|---|---|---|
| Phase | Ingredient | Amount | Amount |
| A | Surfactants | 2.8 | 3.4 |
| | Cetyl Alcohol | 0.5 | 0.6 |
| | Stearyl Alcohol | 0.5 | 1 |
| | Stearic Acid | 3 | 4 |
| | Myristyl Myristate | 2 | 1 |
| | Preservative | 0.25 | 0.4 |
| | Preservative | 0.1 | 0.2 |
| | Mineral Oil | 4 | 4.5 |
| | Beeswax | 1 | 5 |
| | Shorea Robusta Seed Butter | 2 | 1 |
| A2 | Phenethyl Alcohol | 0.02 | 0.04 |
| | Cyclohexasiloxane | 10 | 12 |
| B | Water | QS | QS |
| | Niacinamide (hydrotrope) | 2 | 4 |
| | Caffeine (hydrotrope) | 3 | 1 |
| | Baicalin (antioxidant) | 1 | 5 |
| | Polydatin (antioxidant) | 3 | 2 |
| | Triethanolamine | 0 | 1 |
| | Glycerin | 7 | 10 |
| C | Water | QS | QS |
| D | Acrylonitrile/methylmethacrylate/vinylidene chloride copolymer | 0.2 | 2 |
| E | Acrylamide/Sodium acryloyldimethyltaurate copolymer (and) isohexadecane (and) Polysorbate 80 | 1.9 | 0.5 |
| F | Chlorhexidine Digluconate | 0.25 | 0.3 |
| | Water | QS | QS |
| G | Vitamin E | 1 | 0.5 |

The components of Phase A are combined, mixed, and heated to 75° C. until all ingredients are melted. The components of Phase A2 are separately added and mixed for 10 minutes. The components of Phase B are then slowly added to Phase A/A2 and mixed over a period of 15 minutes, and the mixture is homogenized for 15 minutes. The temperature of the mixture is reduced to 20° C. Phase C is added at a temperature of 45° C. Then Phase D is added at a temperature of 35° C. and the mixture is homogenized for 45 minutes. Finally, Phase E is added and mixed for 5 minutes; Phase F is added and mixed for 5 minutes; and Phase G is added and mixed for 5 minutes.

Example 5

Oil-in-Water Emulsion with SPF

Oil-in-water emulsions containing the antioxidants baicalin and polydatin and the hydrotropes niacinamide and caffeine are presented in the table below.

| Antioxidants (Baicalin and Polydatin) with Hydrotropes (Niacinamide and Caffeine) | | | |
|---|---|---|---|
| Phase | Ingredient | Amount | Amount |
| A | Water | QS | QS |
| | Preservatives | 1.0 | 1.6 |
| | Disodium EDTA | 0.2 | 0.1 |
| | Niacinamide (hydrotrope) | 2 | 5 |
| | Caffeine (hydrotrope) | 3 | 8 |
| | Glycerin | 3 | 3 |
| | Baicalin (antioxidant) | 1 | 8 |
| | Triethanolamine | 0 | 0 |
| | Polydatin (antioxidant) | 3 | 1 |
| | Xanthan Gum | 0.25 | 0.5 |
| B | Dicaprylyl Carbonate | 0.5 | 0.2 |
| | UV Filter Combination | 20 | 30 |
| | Stearic Acid | 2 | 1 |
| | Glycerol Stearate (and) PEG-100 Stearate | 3 | 5 |
| | Cetyl Alcohol | 1 | 1 |
| | Dimethicone | 2 | 3 |
| C | Dimethicone (and) dimethicone/vinyl dimethicone crosspolymer | 1 | 3 |
| D | Ammonium polyacryloyldimethyl taurate | 0.57 | 0.3 |
| E | Water | QS | QS |
| F | Silica | 3 | 1 |
| H | Vitamin E | 1 | 1 |

The components of Phase A are combined and heated to 75° C. while mixing. The components of Phase B are separately combined and slowly added into Phase A while mixing over a period of 15 minutes. Then, the mixture is homogenized for 15 minutes. The temperature of the mixture is reduced to 20° C. Phase C is added to the mixture at a temperature below 50° C. and then homogenized for 10 minutes. Finally, Phase E is added and mixed for 5 minutes; Phase F is added and mixed for 5 minutes; Phase G is added and mixed for 5 minutes; and Phase H is added and mixed for 5 minutes.

Example 6

Water-in-Oil Inverse Emulsion without SPF

Water-in-oil inverse emulsions containing the antioxidants baicalin and polydatin and the hydrotropes niacinamide and caffeine are presented in the table below.

| Antioxidants (Baicalin and Polydatin) with Hydrotropes (Niacinamide and Caffeine) | | | |
|---|---|---|---|
| Phase | Ingredients | Amount | Amount |
| A | Dimethicone | 6 | 4 |
| | Dimethicone (and) dimethicone/vinyl dimethicone crosspolymer | 6 | 8 |
| B | Water | QS | QS |

-continued

Antioxidants (Baicalin and Polydatin) with Hydrotropes (Niacinamide and Caffeine)

| Phase | Ingredients | Amount | Amount |
|---|---|---|---|
|  | Niacinamide (hydrotrope) | 2 | 0.1 |
|  | Caffeine (hydrotrope) | 3 | 2 |
|  | Baicalin (antioxidant) | 1 | 6 |
|  | Polydatin (antioxidant) | 3 | 1 |
|  | Glycerin | 15 | 20 |
|  | Propanediol | 3 | 1 |
|  | Sodium chloride | 0.5 | 0.5 |
|  | Preservative | 1 | 2 |
|  | Sodium citrate | 0.2 | 0.2 |
|  | Disodium EDTA | 0.1 | 0.2 |
| C | Polymethylsilsesquioxane | 0.5 | 1 |
| D | Vitamin E | 1 | 1.5 |

The components of Phase A are combined and mixed until homogenous. The components of Phase B are separately combined using high shear to obtain a clear solution and then the pH of the solution is adjusted to 5.0±0.3. Phase B is then slowly added to Phase A with stirring. After the mixture is homogenous Phase C and Phase D are added and mixed until homogenous.

Example 7

Water-in-Oil Inverse Emulsion with SPF

Water-in-oil inverse emulsions containing the antioxidants baicalin and polydatin and the hydrotropes niacinamide and caffeine are presented in the table below.

Antioxidants (Baicalin and Polydatin) with Hydrotropes (Niacinamide and Caffeine)

| Phase | Ingredient | Amount | Amount |
|---|---|---|---|
| A | Combination of UV Filters | 20 | 21 |
|  | Dimethicone (and) PEG-15/Lauryl polydimethylsiloxyethyl dimethicone crosspolymer | 8.6 | 10 |
|  | Dicaprylyl ether | 5 | 3 |
|  | Silicon | 2 | 5 |
| B | Water | QS | QS |
|  | Niacinamide (hydrotrope) | 2 | 2 |
|  | Caffeine (hydrotrope) | 3 | 3 |
|  | Baicalin (antioxidant) | 1 | 5 |
|  | Polydatin (antioxidant) | 3 | 1 |
|  | Glycerin | 15 | 20 |
|  | Sodium chloride | 0.5 | 0.5 |
|  | Preservatives | 1.5 | 3.8 |
|  | Sodium citrate | 0.2 | 0.2 |
|  | Disodium EDTA | 0.1 | 0.4 |
|  | Propylene glycol | 4 | 0.8 |
| C | Methylmethacrylate crosspolymer | 2 | 3 |
| D | Vitamin A | 1 | 2 |

The components of Phase A are combined and mixed at 75° C.-80° C. The components of Phase B are separated combined and mixed at 75° C.-80° C. Phase B is slowly added into Phase A while mixing; after combined the combination is mixed for 10 minutes. The mixture is cooled to 25° C. and Phase C is added and mixed for about 5 minutes. Finally, Phase D is added and mixed for 5 minutes until the composition is was homogenous.

In the context of the instant disclosure, the phrase "broad spectrum photo protection" refers to protection against at least visible light and/or IR radiation.

In the context of the instant disclosure, the term "full spectrum photo protection" refers to protection against at least UV radiation and to protection against visible light and/or IR ration.

The difference between "broad spectrum photo protection" and "full spectrum photo protection" is that "full spectrum photo protection" necessarily includes protection against UV radiation in addition to protection against visible light and/or IR radiation. "Broad spectrum photo protection," however, includes protection of visible light and/or IR radiation but not necessarily protection against UV radiation. The addition of UV filters to a composition providing "broad spectrum photo protection" would transform the composition into one that provides "full spectrum photo protection" (because the addition of the UV filters allows the composition to provide protection against UV radiation and visible light and/or IR radiation.

The terms "a," "an," and "the" are understood to encompass the plural as well as the singular.

The expression "at least one" means "one or more" and vice versa, and thus includes individual components as well as mixtures/combinations.

The term "about" when referring to a value, is meant specifically that a measurement can be rounded to the value using a standard convention for rounding numbers. For example, "about 1.5" is 1.45 to 1.54. All values set forth herein can be modified with the term "about," if desired to impart the meaning above, or recited without the term, regardless of whether the term "about" is specifically set forth (or is absent) in conjunction with any particular value in the specification.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A method for providing at least broad spectrum photo protection to skin, which includes protection from infrared radiation and visible light, the method comprising topically applying to the skin of a subject a cosmetic composition comprising:
    (a) 0.001 to 20 wt. %, based on the total weight of the composition of one or more antioxidants selected from the group consisting of baicalin, *thermus thermophillus* ferment, ferulic acid, polydatin, silymarin, punica granatum extract, mango leaf extract, catechin, hesperetin, astilbin, and DHC V;
    (b) 0.001 wt. % to 30 wt. % of one or more cosmetically acceptable hydrotropes selected from the group consisting of nicotinamide, caffeine, sodium PCA, sodium salicylate, urea, and hydroxyethyl urea; and
    (c) a cosmetically acceptable carrier;
       wherein the combination of (a), (b), and (c) alone provides at least broad spectrum protection from both infrared radiation and visible light.

2. The method of claim 1, wherein the one or more antioxidants of (a) comprises baicalin.

3. The method of claim 1 where the one or more antioxidants of (a) comprises polydatin.

4. The method of claim 1, further comprising:
(d) 0.001 to 10 wt. %, based on the total weight of the compositions, of one or more nonionic emulsifiers.

5. The method of claim 4, wherein the nonionic emulsifier is selected from a polyol ester, a glycerol ether, an oxyethylenated, an oxypropylenated ether, an ethylene glycol polymer, and combinations thereof.

6. The method of claim 5, wherein the nonionic emulsifier comprises a combination of a polyol ester and an ethylene glycol polymer.

7. The method of claim 1, further comprising:
(e) one or more UV filters.

8. The method of claim 7, wherein the total amount of the one or more UV filters of (e) is 0.001 to 30 wt. %, based on the total weight of the composition.

9. The method of claim 7, wherein the one or more UV filters of (e) are selected from the group consisting of a para-aminobenzoic acid derivative, a salicylic derivative, a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, and a chalcone.

10. The method of claim 1, wherein the cosmetically acceptable carrier of (c) comprises water, an organic solvent, or a mixture thereof.

11. The method of claim 1, further comprising:
(f) one or more skin active ingredients.

12. The method of claim 1, wherein the composition further comprises:
(g) one or more silicon oils.

13. The method of claim 12, wherein the one or more silicon oils of (g) are selected from the group consisting of polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes and (2-phenylethyl)trimethylsiloxysilicates.

14. The method of claim 11, wherein the one or more silicone oils of (g) comprises dimethicone.

15. A method for providing at least broad spectrum photo protection to skin, which includes protection from infrared radiation and visible light, the method comprising topically applying to the skin of a subject a cosmetic composition comprising:
(a) 0.001 to 20 wt. %, based on the total weight of the composition, of one or more antioxidants selected from the group consisting of baicalin, polydatin, *thermus thermophillus* ferment, and punica granatum extract;
(b) 0.001 wt. % to 30 wt. %, based on the total weight of the composition, of one or more cosmetically acceptable hydrotropes selected from the group consisting of nicotinamide, caffeine, sodium PCA, sodium salicylate, urea, and hydroxyethyl urea;
(c) a cosmetically acceptable carrier selected from the group consisting of water and an organic solvent;
(d) 0.001 to 10 wt. %, based on the total weight of the composition, of one or more nonionic emulsifiers; and
(e) one or more UV filters;
wherein the combination of (a), (b), and (c) alone provides at least broad spectrum protection from both infrared radiation and visible light.

16. The method of claim 15, wherein the cosmetic composition comprises both nicotinamide and caffeine.

17. The method of claim 16, wherein the one or more antioxidants of (a) comprises baicalin.

18. The method of claim 16, wherein the one or more antioxidants of (a) comprises polydatin.

19. The method of claim 16, wherein the one or more antioxidants of (a) comprises *thermus thermophillus* ferment.

20. The method of claim 16, wherein the one or more antioxidants of (a) comprises punica granatum extract.

* * * * *